(12) United States Patent
Kuo et al.

(10) Patent No.: US 8,464,378 B2
(45) Date of Patent: Jun. 18, 2013

(54) MEDICAL INSPECTION APPARATUS

(75) Inventors: Po-Hsiu Kuo, Taoyuan County (TW);
Yu-Ching Ni, Taoyuan County (TW);
Meei-Ling Jan, Taoyuan County (TW)

(73) Assignee: Institute of Nuclear Energy Research Atomic Energy Council, Taoyuan County (TW)

(*) Notice: Subject to any disclaimer, the term of this patent is extended or adjusted under 35 U.S.C. 154(b) by 25 days.

(21) Appl. No.: 13/178,604

(22) Filed: Jul. 8, 2011

(65) Prior Publication Data

US 2012/0029338 A1 Feb. 2, 2012

(30) Foreign Application Priority Data

Jul. 27, 2010 (TW) .............................. 99124682 A

(51) Int. Cl.
*A61G 13/00* (2006.01)
(52) U.S. Cl.
USPC ................... 5/600; 5/601; 600/437; 600/473; 601/41; 378/37
(58) Field of Classification Search
USPC .... 600/437, 431; 5/600, 601; 601/41; 378/37
See application file for complete search history.

(56) References Cited

U.S. PATENT DOCUMENTS

| 4,341,222 | A  | * | 7/1982  | Gardineer et al. | 600/437 |
|-----------|----|---|---------|------------------|---------|
| 5,820,552 | A  |   | 10/1998 | Crosby et al.    |         |
| 6,419,390 | B1 |   | 7/2002  | Landis-Lowell    |         |
| 7,908,690 | B2 | * | 3/2011  | Luginbuhl et al. | 5/601   |
| 8,218,723 | B2 | * | 7/2012  | Ein-Gal          | 378/37  |
| 2002/0056160 | A1 | * | 5/2002  | Falbo et al.    | 5/600   |
| 2007/0276298 | A1 | * | 11/2007 | Sebelius et al. | 601/41  |
| 2008/0103387 | A1 | * | 5/2008  | Gross            | 600/424 |
| 2010/0234727 | A1 | * | 9/2010  | Yoshizawa et al. | 600/431 |
| 2011/0007868 | A1 | * | 1/2011  | Ein-Gal          | 378/37  |

\* cited by examiner

*Primary Examiner* — Tse Chen
*Assistant Examiner* — Baisakhi Roy
(74) *Attorney, Agent, or Firm* — WPAT, PC; Justin King

(57) ABSTRACT

A medical inspection apparatus includes a main body and an inspection module. The main body has at least two guide rails and at least two sliding blocks which are slidably coupled to the guide rails respectively, and the inspection module further includes at least one pivot, and each of the sliding blocks is pivotally connected to the inspection module with a pivot, so that the inspection module is capable of sliding on the sliding rail to regulate the height and rotating with respect to the pivot to regulate the inclination. Moreover, the main body has a first supporting component and a second supporting component, so that the combination of the first supporting component and the second supporting component can provide three-ended support for an inspected person.

13 Claims, 3 Drawing Sheets

MEDICAL INSPECTION APPARATUS

BACKGROUND OF THE INVENTION

1. Field of Invention

The present invention relates to an inspection apparatus, and more particularly to a medical inspection apparatus capable of having its inclination and height regulated and providing three-ended support for an inspected person.

2. Related Art

After entering the $21^{st}$ century, the national income is increasing and the living standard of the people is rising. However, with the transition of the cultural and living background, the environment, and the society, the incidence of cancer, especially the breast cancer, grows every year and the affected group of people tends to be younger. Thus, it is extremely important to use sophisticated imaging instruments and facilities to discover the breast cancer at the early stage and arrange for appropriate treatment to increase the cure rate, thereby saving the medical resources and reducing the social cost. In the prior art, the breast image examination and evaluation can be implemented by using the following technologies such as mammography, sonography, magnetic resonance imaging (MRI), and nuclear medicine (positron or single photon) computer tomography imaging. These technologies assist the physicians in diagnosis and evaluation, so as to increase the probability of discovering the breast diseases and to provide correct treatment.

The current inspection apparatuses are classified into standing-type, sitting-type, and lying-type apparatuses. No matter which type of the inspection apparatus is used, the inspected person may feel uncomfortable as the body pressure is concentrated on one side after keeping a gesture for a long time during the inspection, so that the inspected person needs to move from time to time to relieve the body pressure, which may result in an undesirable breast image and cause problems like error interpretation. Moreover, the structure of the standing-type apparatus has a high center of gravity and thus needs to be fixed on the ground; while the structure of the lying-type apparatus needs to be equipped with a platform for supporting the inspected person, and thus has a large volume and is inconvenient to move, so that the inspected person needs to go to the medical institution for inspection, and these types of inspection apparatuses are difficult to be promoted.

In addition, when the standing-type or sitting-type apparatus is used, the breast of the inspected person is placed on an inspection surface, so that it is difficult to position and concentrate the breast, and dead space exist in the inspection of breast tissues close to the chest wall, which is easy to miss lesions. When the lying-type apparatus is used, the inspected person needs to lie on the support platform, and the platform bears the weight of the whole body. As it is specified in the medical safety regulations that the load mechanical strength needs to reach a safety factor 4 (taking a platform load of 200 kg for example, the safety factor 4 means a load of 800 kg), the support plate is made much thicker, and the inspection range is reduced, which affects the correctness of the inspection result.

U.S. Pat. No. 6,419,390 B1 "FOLDING MAMMOGRAPHY TABLE AND METHOD OF USE" discloses a folding table used in a breast inspection apparatus. The table includes an upper base and a lower base, a mechanism capable of adjusting the height of the upper base over the lower base to accommodate an inspected person, and a mechanism capable of folding the upper base down to a horizontal position However, this technology does not provide any support for the lower half of the body of the inspected person, and the inspected person needs to stand on his/her own feet, which is rather inconvenient for those with limited activity, for example, the handicapped or the palsied.

U.S. Pat. No. 5,820,552 "SONOGRAPHY AND BIOPSY APPARATUS" also discloses a breast inspection apparatus, which includes an inclinable inspection module and a base for supporting an inspected person. Although the apparatus provides a support base to support the inspected person, the support mode is not three-ended support, and thus when the inclination of the inspection apparatus is regulated, the inspected person, for example, the handicapped or the palsied, may fall from the base for lack of support due to the weak legs.

SUMMARY OF THE INVENTION

The present invention is directed to a medical inspection apparatus, capable of having the inclination and height of its inspection module regulated and providing three-ended support for an inspected person. Thereby, the medical inspection apparatus relieves the discomfort of the inspected person by lowering the concentrated body pressure on one side, and ensures that the inspected person keeps a gesture during the inspection, so as to solve the problems like error interpretation caused by an undesirable breast image resulting from the fact that the inspected person may move from time to time to relieve the concentrated body pressure on one side after standing or lying for a long time during the inspection.

The present invention is directed to a medical inspection apparatus. When the apparatus is used, the inspected person leans forward to make the breast tissue naturally hang and concentrated under the gravity effect, and the breast resting at the fixed part of the inspection module passes through an elastically extensible element on the inspection module.

As the elastically extensible element is made of a thin, elastic, and soft material, when the inspector unit is lifted to contact the thin elastic material, the elastic material deforms according to the shape of the human body, such that the inspection module is closer to the chest wall of the inspected person, thus significantly increasing the effective inspection range, and solving the dead space problem in the inspection caused by the thickness of the plate in the prior art.

The present invention provides a medical inspection apparatus, which includes a main body and an inspection module. The main body has at least two linear moving units, respectively disposed at two sides of the main body. The main body further includes a first supporting component and a second supporting component. The first supporting component is used for supporting the knees of an inspected person, and the second supporting component is used for supporting the hips and legs of the inspected person.

Thus, the combination of the first supporting component and the second supporting component provides three-ended support for the inspected person, and due to the characteristic of the three-ended support, the inspected person who is weak below the waist is enabled to successfully go through the inspection with the support of an external force. In addition, the inspection module is respectively pivotally connected to the at least two linear moving units, so that the inspection module may have the height and the inclination regulated to reach an appropriate inspection position through a linear displacement movement provided by the linear moving units and a rotary movement.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

In order to make the characteristics, objectives, and efficacies of the present invention comprehensible to the Examiner, relative detailed structures and design concepts of the apparatus of the present invention are described in detail below, so that the Examiner can better understand the features of the present invention.

Figure 1:
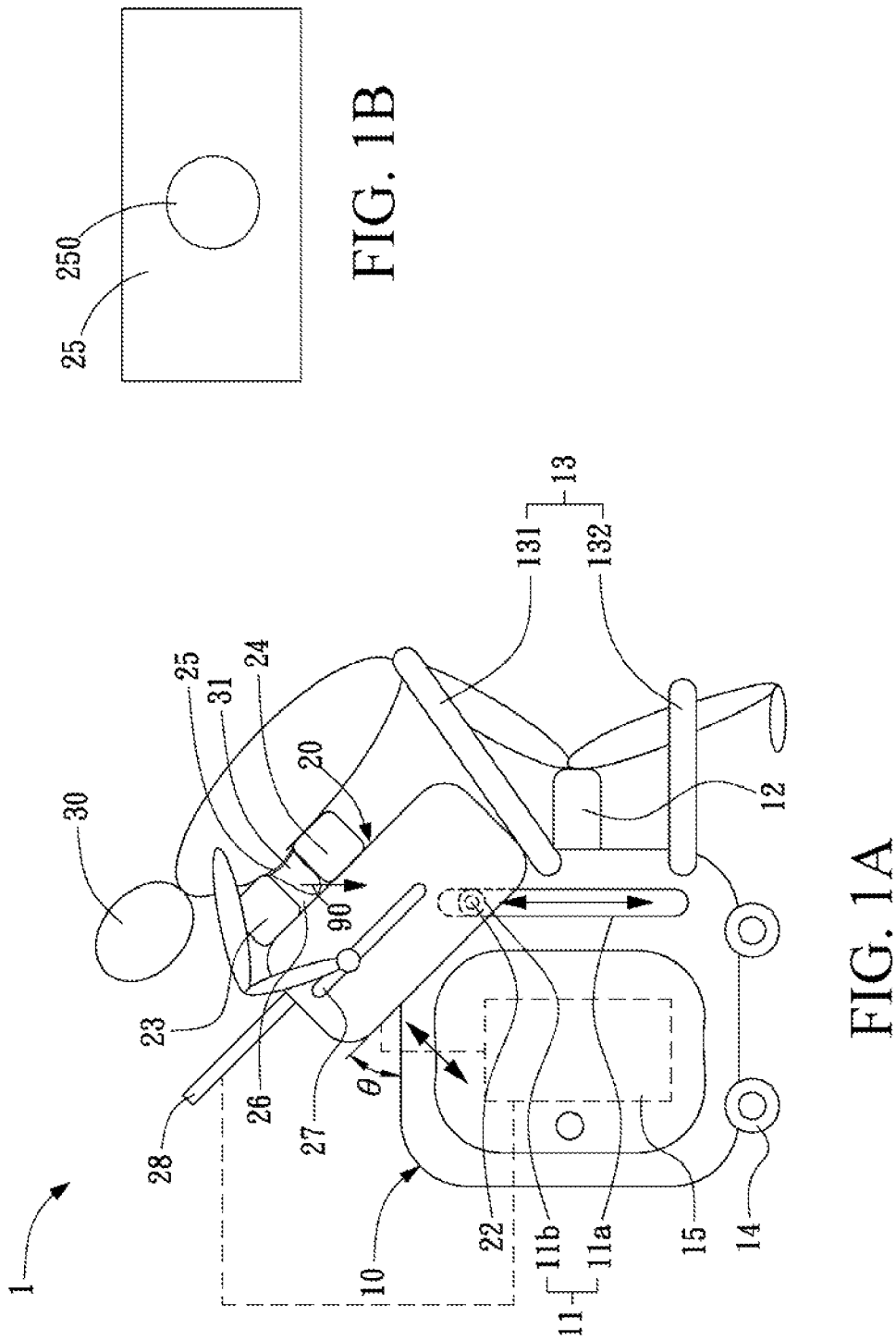
FIG. 1A is a schematic structural view of a first embodiment of a medical inspection apparatus according to the present invention.
FIG. 1B is a schematic front view of an elastically extensible element according to the present invention.

FIG. 1A is a schematic structural view of a first embodiment of a medical inspection apparatus according to the present invention. In this embodiment, the medical inspection apparatus 1 includes a main body 10 and an inspection module 20. The main body 10 has at least two linear moving units 11, respectively disposed at two sides of the main body 10.

The main body 10 further includes a first supporting component 12 and a second supporting component 13. The first supporting component 12 is used for supporting the knees of an inspected person 30, and the second supporting component 13 is used for supporting the hips and legs of the inspected person 30. In addition, the inspection module 20 is respectively pivotally connected to the at least two linear moving units 11, so that the inspection module 20 has the height and the inclination regulated to reach an appropriate inspection position (indicated by arrows in FIG. 1A) through a linear displacement movement provided by the linear moving units 11 and a rotary movement. The regulation of the height and the inclination of the inspection module 20 may be implemented in an electrical control mode or manually carried out by disposing a handlebar 27 at one side or respectively at two sides of the inspection module 20.

In this embodiment, the second supporting component 13 further includes a first elastic belt 131 and a second elastic belt 132, respectively used for binding the hips and legs of the inspected person 30, for example, as shown in FIG. 1A, the first elastic belt 131 is used for binding and securing the hips of the inspected person 30, and the second elastic belt 132 is used for binding and securing the legs of the inspected person 30. Thereby, the combination of the first supporting component 12 and the second supporting component 13 provides three-ended support for the inspected person 30, and due to the characteristic of the three-ended support, the inspected person 30 who is weak below the waist, for example but not limited to, the handicapped or the palsied, is enabled to successfully go through the inspection with the support of an external force.

In this embodiment, each linear moving unit 11 further has a guide rail 11a and a sliding block 11b slidably coupled to the guide rail 11a, and two ends of the inspection module 20 are respectively pivotally connected to the corresponding sliding blocks 11b via a pivot 22. In this embodiment, the inspection module 20 further includes at least two inspection components, and only two are shown in FIG. 1A, that is, a first inspection component 23 and a second inspection component 24. The two inspection components 23 and 24 form a recessed space 26, an elastically extensible element 25 is further disposed on the recessed space 26, for example, a piece of elastically extensible cloth, and an opening 250 is formed in the elastically extensible element 25, as shown in FIG. 1B. The recessed space 26 can be used for accommodating a tissue to be inspected of the inspected person 30, for example, the breast, hand, leg, or brain. The tissue to be inspected of this embodiment is a breast 31.

Moreover, the elasticity of the elastically extensible element 25 can be used to bear the part of the tissue difficult to be inspected of the inspected person, for example, the axilla, and due to the elasticity of the elastically extensible element 25, the axilla tissue can be accommodated in the recessed space 26, so that the body parts of the inspected person are inspected. For example, assume that the tissue to be inspected is the breast 31, and an inclined angle θ is formed between the inspection module 20 and the main body 10. When the breast 31 passes through the opening, as the human body is lying face down over the inspection module 20, the chest wall of the human body close to the breast 31 can be closely attached to the elastically extensible element 25, and the elastically extensible element 25 deforms according to the shape of the human body, such that the first inspection component 23 and the second inspection component 24 of the inspection module 20 are made closer to the chest wall of the inspected person, thereby significantly increasing the effective inspection range and reducing the dead angles of the inspection. When the breast 31 passes through the opening 250 and is accommodated in the recessed space 26, the gravity 90 is acting on the breast 31 due to the inclined angle, so as to increase the inspected area of the breast 31. The inspection module 20 may be, but not limited to, an inspection module capable of detecting a positron emitter, a single photon, or an X-ray.

In this embodiment, the main body 10 further includes an inspection signal processing unit 15, which is electrically connected to the inspection module 20, and used for processing an inspection signal of the inspection module 20 to generate an inspection image signal. The inspection module 20 further includes a display 28, which is electrically connected to the inspection signal processing unit 15, and used for receiving the inspection image signal and displaying an inspection image related to the inspection image signal. Further, in another embodiment, the display 28 may also play films, for example, movies, audio-visual animations, or music that can relax the body and mind of the inspected person or divert the attention of the inspected person. In this embodiment, the main body 10 further includes a plurality of wheels 14. As the inspection signal processing unit 15 is integrally formed with the main body, the inspected person 30 and the inspection personnel or physician can immediately view the image, and thus the inspection personnel or physician can make evaluation or explain to the inspected person 30 right away. In addition, as the inspection signal processing unit 15 is integrally formed with the main body 10, and the wheels 14 are added to the main body 10 to enable the main body to move, the medical inspection apparatus of the present invention achieves high moving flexibility and signal processing capability.

Figure 2:
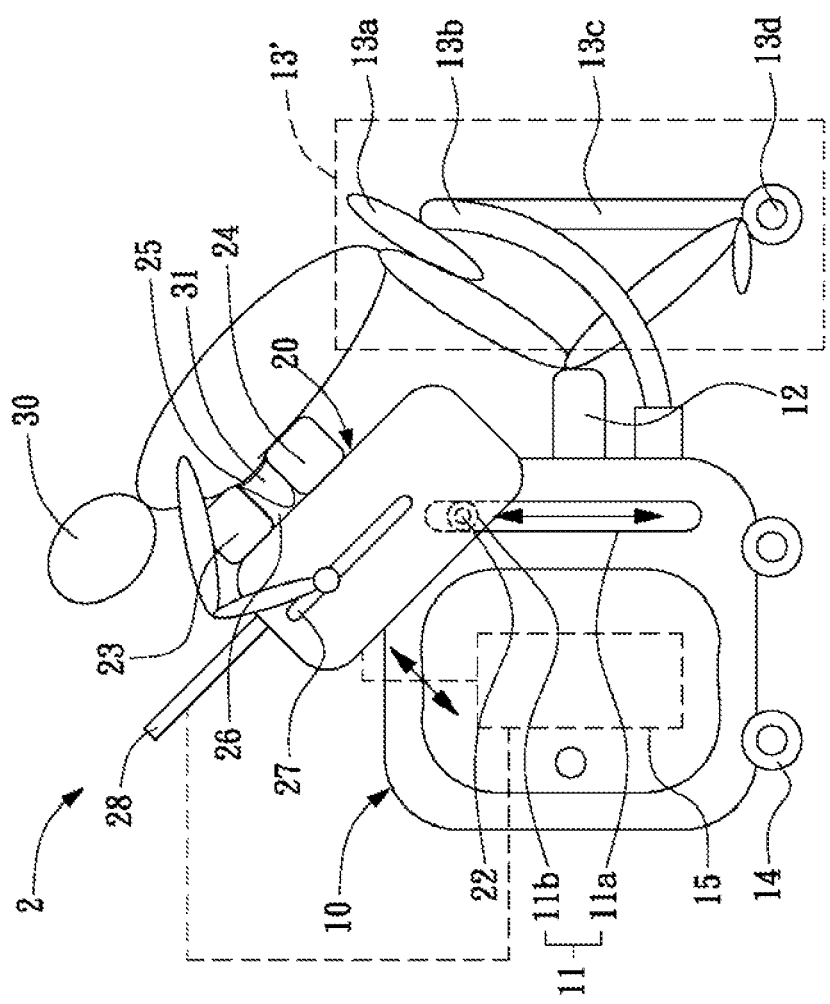
FIG. 2 is a schematic structural view of a second embodiment of a medical inspection apparatus according to the present invention.

FIG. 2 is a schematic structural view of a second embodiment of a medical inspection apparatus according to the present invention. The only difference between the medical inspection apparatus 2 of this embodiment and the medical inspection apparatus 1 of the first embodiment lies in the second supporting component 13'. The second supporting component 13' further includes a base 13a, the base 13a is connected to the main body 10 through a connecting member 13b, and the base 13a has a supporting member 13c for supporting against the ground. One end of the supporting member 13c contacting the ground is further disposed with at least one wheel 13d. In this embodiment, the base 13a provides support for the hips of the inspected person 30, and the ground provides support for the legs of the inspected person 30. Thereby, the combination of the first supporting component 12 and the second supporting component 13' provides three-ended support for the inspected person 30, and due to the characteristic of the three-ended support, the inspected person 30 who is weak below the waist, for example but not limited to, the handicapped or the palsied, is enabled to successfully go through the inspection with the support of an external force.

Figure 3:
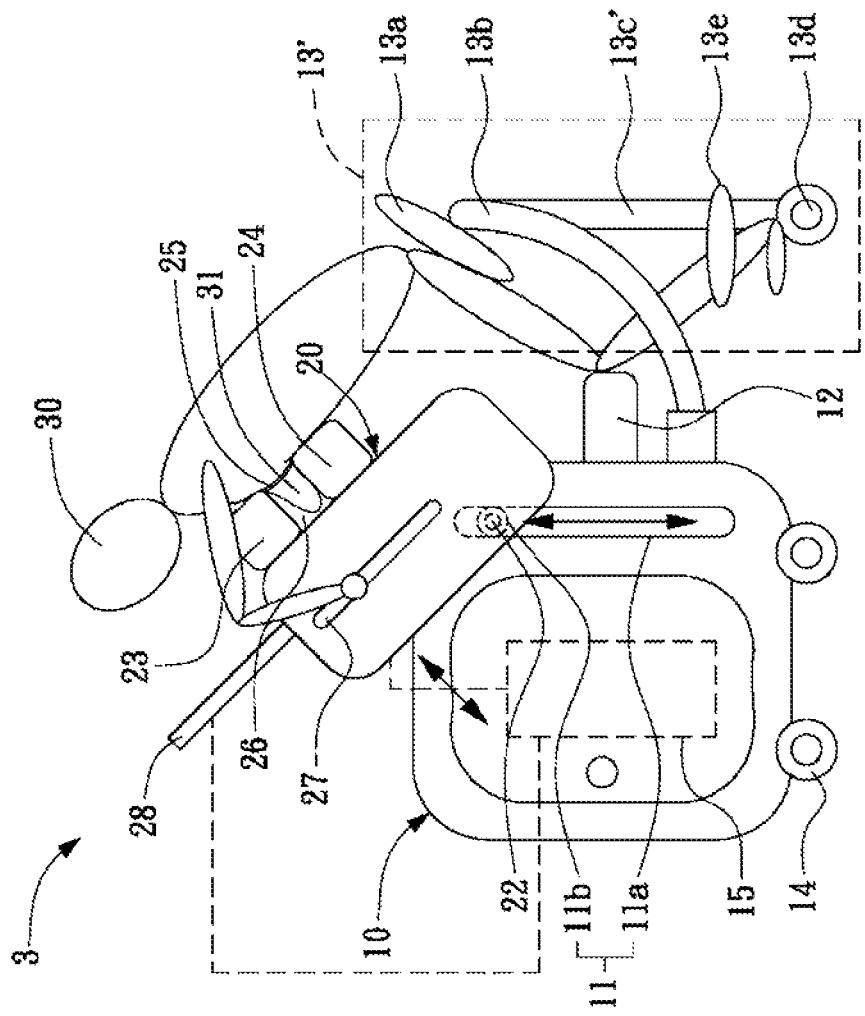
FIG. 3 is a schematic structural view of a third embodiment of a medical inspection apparatus according to the present invention.

FIG. 3 is a schematic structural view of a third embodiment of a medical inspection apparatus according to the present invention. The only difference between the medical inspection apparatus 3 of this embodiment and the medical inspection apparatus 2 of the second embodiment lies in the supporting member 13c' of the second supporting component 13'. One end of the supporting member 13c' is further provided with an elastic belt 13e, for binding and securing the feet or the legs of the inspected person 30 to the supporting member 13c'. In this embodiment, the base 13a provides support for the hips of the inspected person 30, the combination of the supporting member 13c' and the elastic belt 13e provides support for the legs of the inspected person 30, and the first supporting component 12 provides support for the knees of the inspected person 30. Thereby, the combination of the first supporting component 12 and the second supporting component 13' provides three-ended support for the inspected person 30, and due to the characteristic of the three-ended support, the inspected person 30 who is weak below the waist, for example but not limited to, the handicapped or the palsied, is enabled to successfully go through the inspection with the support of an external force.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

In view of the above, in the medical inspection apparatus of the present invention, the position of the inspector unit can be regulated, to inspect the chest of an individual inspected person when the inspected person is in a status of not lying face up (for example, lying face down or standing upright), so as to acquire a precise inspection result for subsequent analysis. Therefore, the industrial competitiveness is enhanced and the development of peripheral industries is promoted. As such, the present invention already meets the requirements for filing a patent application as set forth in the Patent Act. Thus, the application for an invention patent is filed according to the law. We will be most grateful if the Examiner can find time to conduct the examination and grant a patent right.

What is claimed is:

1. A medical inspection apparatus for examining a patient, comprising:
    a main body, having at least two linear moving units, respectively disposed at two sides of the main body;
    a first supporting component, for supporting knees of the patient;
    a second supporting component, for supporting hips and legs of the patient; and
    an inspection module, coupled to the main body by directly pivotally connecting to the at least two linear moving units with connecting pivots, wherein the at least two linear moving units move the inspection module in a linear movement by moving the connecting pivots, and the inspection module pivots around the connecting pivots.

2. The medical inspection apparatus according to claim 1, wherein the second supporting component further comprises a first belt and a second elastic belt, respectively used for binding the hips and legs of the inspected person.

3. The medical inspection apparatus according to claim 1, wherein the second supporting component further comprises a base, the base is connected to the main body through a connecting member, and the base has a supporting member for supporting against the ground.

4. The medical inspection apparatus according to claim 3, wherein one end of the supporting member is further provided with an elastic belt, for binding and securing the feet or the legs of the inspected person to the supporting member.

5. The medical inspection apparatus according to claim 3, wherein the supporting member further comprises at least one wheel.

6. The medical inspection apparatus according to claim 1, wherein the inspection module further comprises at least two inspection components, and the at least two inspection components form a recessed space.

7. The medical inspection apparatus according to claim 6, wherein an inclined angle is formed between the inspection module and the main body, the inspection module further comprises an elastically extensible element disposed on the recessed space, and an opening is formed in the elastically extensible element, such that when a tissue to be inspected passes through the opening and is accommodated in the recessed space, the gravity is acting on the tissue to be inspected due to the inclined angle, so as to increase the inspected area of the tissue to be inspected.

8. The medical inspection apparatus according to claim 1, wherein the main body further comprises a plurality of wheels.

9. The medical inspection apparatus according to claim 1, wherein each linear moving unit further has a guide rail and a sliding block slidably coupled to the guide rail, and two ends of the inspection module are respectively pivotally connected to the corresponding sliding blocks via a pivot.

10. The medical inspection apparatus according to claim 1, wherein the main body further comprises an inspection signal processing unit, electrically connected to the inspection module, and used for processing an inspection signal of the inspection module to generate an inspection image signal.

11. The medical inspection apparatus according to claim 10, wherein the inspection module further comprises a display, electrically connected to the inspection signal processing unit, and used for receiving the inspection image signal and displaying an inspection image related to the inspection image signal.

12. The medical inspection apparatus according to claim 1, wherein the inspection module further comprises a display for playing a film.

13. The medical inspection apparatus according to claim 1, wherein the inspection module is an inspection module capable of detecting positron, single photon, or X-ray signals.

* * * * *